United States Patent
Lieberman et al.

(10) Patent No.: US 6,669,342 B2
(45) Date of Patent: *Dec. 30, 2003

(54) METHOD FOR DIAGNOSING AND IMPROVING VISION

(75) Inventors: David M. Lieberman, New York, NY (US); Jonathon Grierson, Atwater, OH (US)

(73) Assignee: Scientific Optics, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/154,412

(22) Filed: May 22, 2002

(65) Prior Publication Data

US 2003/0055412 A1 Mar. 20, 2003

Related U.S. Application Data

(63) Continuation of application No. 09/646,739, filed as application No. PCT/US99/23209 on Oct. 1, 1999, now Pat. No. 6,416,179.
(60) Provisional application No. 60/102,813, filed on Oct. 2, 1998.

(51) Int. Cl.⁷ ................................. A61B 3/10
(52) U.S. Cl. ..................................... 351/212
(58) Field of Search ................. 351/205, 206, 351/212, 219, 160 R, 177, 161; 606/4, 5, 166

(56) References Cited

U.S. PATENT DOCUMENTS 4,861,152 A * 8/1989 Vinzia .................. 351/161

* cited by examiner

*Primary Examiner*—George Manuel
(74) *Attorney, Agent, or Firm*—Darby & Darby (57) ABSTRACT

Methods, and apparatus are disclosed for performing corneal ablation procedures of the eye (12) in a manner which does not interfere with the natural shape of the cornea or its orientation relative to the remainder of the eye, but which changes its surface curvature appropriately to achieve the required correction of vision. Three preferred embodiments are described, which model the cornea to different degrees of accuracy. Once the model of the cornea is obtained (610, 620, 630), surface curvature is modified (650) to achieve the degree of correction in refraction that is necessary, as determined by an eye test of the patient. The modified model of the cornea is then utilized to control the removal of material from the surface of the cornea in a corneal ablation operation.

9 Claims, 11 Drawing Sheets

METHOD FOR DIAGNOSING AND IMPROVING VISION

This is a continuation of application Ser. No. 09/646,739, filed Sep. 19, 2000. Application Ser. No. 09/646,739 was the U.S. national stage of International application PCT/US99/23209, published in English, and claimed the benefit of provisional application No. 60/102,813 filed Oct. 2, 1998. Each of these prior applications is hereby incorporated herein by reference, in its entirety.

FIELD OF THE INVENTION

The present invention relates to a method and system for diagnosing improving the vision of an eye.

BACKGROUND OF THE INVENTION

Most common defects in human vision are caused by the inability of the eye to focus properly. For example, near-sightedness can be attributed to an eye which focuses forward of the retina instead of on it, farsightedness can be attributed to an eye which focuses beyond the retina, and astigmatism can be attributed to an eye which cannot produce a sharp focus, instead producing an area of blurriness. Ophthalmologists model the cornea as a portion of an ellipsoid defined by orthogonal major and minor axes. Current surgical procedures for correcting visual acuity are typically directed at increasing or decreasing the surface curvature of the cornea, while making its shape more spherical.

In conjunction with modern corneal procedures, such as corneal ablation surgery, and for clinical applications, high resolution cameras are used to obtain a digitized array of discrete data points on the corneal surface. One system and camera useful for mapping the cornea is the PAR Corneal Topography System (PAR CTS) available from PAR Vision Systems. The PAR CTS maps the corneal surface topology in two-dimensional Cartesian space, i.e., along x- and y-coordinates, and locates the "line-of-sight", which is then used by the practitioner to plan the surgical procedure. The "line-of-sight" is a straight line segment from a fixation point to the center of the entrance pupil. As described more fully in Mandell, "Locating the Corneal Sighting Center From Videokeratography," J. Refractive Surgery, V. 11, pp. 253–259 (July/August 1995), a light ray which is directed toward a point on the entrance pupil from a point of fixation will be refracted by the cornea and aqueous and pass through a corresponding point on the real pupil to eventually reach the retina.

The point on the cornea at which the line-of-sight intersects the corneal surface is the "optical center" or "sighting center" of the cornea. It is the primary reference point for refractive surgery in that it usually represents the center of the area to be ablated in photorefractive keratectomy. The line-of-sight has conventionally been programmed into a laser control system to govern corneal ablation surgery. However, some surgeons prefer to use the pupillary axis as a reference line. Experienced practitioners have employed various techniques for locating the sighting center. In one technique, the angle lambda is used to calculate the position of the sighting center relative to the pupillary ("optic") axis. See Mandell, supra, which includes a detailed discussion of the angles kappa and lambda, the disclosure of which is incorporated herein by reference as if set forth in its entirety herein.

In current corneal ablation procedures, a portion of the corneal surface is ablated. The gathered elevational data is used to direct an ablation device such as a laser so that the corneal surface can be selectively ablated to more closely approximate a spherical surface of appropriate radius about the line-of-sight, within the ablation zone. The use of the line-of-sight as a reference line for the procedures may reduce myopia or otherwise correct a pre-surgical dysfunction. However, a more irregularly shaped cornea may result, which may exacerbate existing astigmatism or introduce astigmatism in the treated eye. This will complicate any subsequent vision correction measures that need be taken. Also, any substantial surface irregularities which are produced can cause development of scar tissue or the local accumulation of tear deposits, either of which can adversely affect vision.

Implicit in the use of the-line-of sight or the pupillary axis as a reference axis for surgical procedures is the assumption that the cornea is symmetric about an axis extending along a radius of the eye. The cornea, however, is an "asymmetrically aspheric" surface. "Aspheric" means that the radius of curvature along any corneal "meridian" is not a constant (a "meridian" could be thought of as the curve formed by the intersection of the corneal surface and a plane containing the pupillary axis). Indeed, the corneal curvature tends to flatten progressively from the geometric center to the periphery. "Asymmetric" means that the corneal meridians do not exhibit symmetry about their centers. The degree to which the cornea is aspheric and/or asymmetrical varies from patient to patient and from eye to eye, within the same person.

Clinical measurements performed with the PAR CTS, as analyzed in accordance with the method disclosed in U.S. Pat. No. 5,807,381 assigned to the assignee of the present patent application, reveal that the cornea exhibits a tilt, typically a forward and downward tilt, relative to the eye. This tilt may be as great as 6° and, on the average, is between 1° and 3°. Hence, a corneal ablation procedure which utilizes the line-of-sight or pupillary axis as a reference axis tends to over-ablate some portions of the cornea and underablate other portions of the cornea. At the same time, it changes the geometric relationship between the cornea and the remainder of the eye. Thus, any ablation procedure which does not take into account the tilt of the cornea is not likely to achieve the desired shaping of the cornea and may therefore be unpredictable in its effect.

Analysis of clinical measurements in accordance with the method of U.S. Pat. No. 5,807,381 also reveals that the point on the surface of the cornea which is most distant from the reference plane of the PAR CTS (hereafter referred to as the HIGH point) is a far more effective reference point for corneal ablation than the center of the cornea. Specifically, as demonstrated in U.S. Pat. No. 5,807,381 laser ablation about an axis passing through the HIGH point produces a much more regularly shaped cornea and removes substantially less corneal material than the same operation performed about an axis close to the center of the eye, such as the pupillary axis.

Although incorporating corneal tilt and utilizing the HIGH point leads to improved and more consistent results with corneal ablation surgery, there is still an excessively high degree of unpredictability. For example, recent analyses of clinical measurements have revealed that the post-operative cornea begins to change shape a short time after corneal ablation surgery. Thus, a nearly perfectly spherical post-operative cornea, will, over time, return to an aspheric, asymmetric shape.

The use of a collagen gel has been proposed as a vehicle to facilitate smoothing of the corneal undulations. See Ophthalmology Times, "*Slick Start, Clear Finish,*" 1995, pp. 1 and 24 (Jun. 19–25, 1995) and Review of Ophthalmology, "*News & Trends: Researchers Unveil New Ablatable Mask,*" pp. 12–13 (June 1995), the disclosures of which are incorporated herein by reference as if set forth in their entirety herein. A Type 1 collagen is molded between a contact lens and the anterior surface of the cornea to form a gel mask. The surgeon can adjust the curvature of the postoperative cornea by selecting a flatter or steeper lens, as desired. Reportedly, the gel mask does not shift when hit by laser pulses. Therefore, instead of selective ablation of predetermined locations of the cornea, the masked cornea can be ablated to a uniform depth, thereby conforming the surface contour of the cornea to the lens. A smooth postoperative cornea results, and refractive power correction can be achieved. However, because the ablation operation is centered on the optical center of the cornea or the center of the pupil and does not allow for corneal tilt, the postoperative eye may exhibit an irregular shape or more corneal material may be removed than is necessary.

What is needed in the art and has heretofore not been provided is a method of correcting vision that avoids one or more of these problems, that can produce predictable results, and that provides corrected vision with respect to the particular topology of the patient's eye on which the correction is being performed.

It is therefore one object of the present invention to provide a method for improving the vision of an eye.

It is an additional object of the present invention to provide an improved surgical method for a corneal ablation procedure.

It is also an object of the present invention to provide a method and apparatus for diagnosing and analyzing a pre-surgical eye for the purpose of predicting the post-operative condition of the eye and planning more effective surgery.

The present inventors believe that corneal ablation surgery has had limited success and predictability, because of a parochial approach. The conventional wisdom has been to concentrate on the shape of the cornea, with the expectation that a smooth, spherical cornea will optimize vision. However, the human eye is a complex system which includes numerous optical components besides the anterior surface of the cornea (for example, the posterior corneal surface, the lens and the aqueous), all of which affect vision. Also, the mechanical environment of the eye cannot be ignored. For example, recent analyses of clinical measurements reveal that the eyelids exert substantial pressure on the cornea, causing it to flatten near its upper margin and to form a depression near its lower margin. It is believed that the mechanical environment of the eye accounts, in large part, for its shape. This also explains why a perfectly spherical post-operative cornea would return to an aspherical, asymmetric shape.

In accordance with the present invention, corneal ablation procedures of the eye are performed in a manner which does not interfere with the natural shape of the cornea or its orientation relative to the remainder of the eye, but which changes its surface curvature appropriately to achieve the required correction of vision. Three preferred embodiments are described, which model the cornea to different degrees of accuracy. Once the model of the cornea is obtained, surface curvature is modified to achieve the degree of correction in refraction that is necessary, as determined by an eye test of the patient. The modified model of the cornea is then utilized to control the removal of material from the surface of the cornea in a corneal ablation operation.

In a first embodiment, the cornea is modeled as an ellipsoid having major and minor axes which are perpendicular to each other. These are the axes that are revealed by conventional eye tests as being appropriate for correction of refraction. On a model of the cornea generated in accordance with disclosure of U.S. Pat. No. 5,807,381 perpendicular planes are constructed which contain the local or tilted Z axis and are rotated about that axis to the angle specified by the eye test. The intersection of each of these planes with the surface model produces an arcuate curve. Each of these curves is then estimated by a circular arc which estimates the patient's current radius of curvature at each axis. A modified arc is then determined which achieves the required diopter correction at each axis. A model of the post-operative cornea is then created by performing a smooth interpolation from one of the arcs to the other. In this model, the corneal surface is represented as the surface of an ellipsoid which has the corrected radii of curvature at the two orthogonal axes specified by the eye test.

In an second embodiment, the cornea is modeled in such a manner as to preserve its asymmetry. To achieve this, a large number of annularly spaced meridians are generated on the surface model of the cornea. The distance along each meridian is measured from the HIGH point to the perimeter of the working area of the cornea, and the curves with the greatest and least average radius of curvature are each estimated by a circular arc. The complementary curves corresponding to the two initial curves (i.e. those extending from the HIGH point diametrically opposite to the corresponding curve are then also estimated by circular arcs. Each of the four arcs is then adjusted for curvature to achieve the desired degree of visual correction at each arc. The model of the post-operative cornea is then generated by angularly interpolating between pairs of the four arcs mentioned above and providing smoothing between two partial surfaces at each of the four initial arcs.

A third embodiment of the invention comes closest to preserving the initial shape of the cornea. Initially, a large number of angularly spaced meridians, for example 72, are generated on the surface model. The curves defining the meridians, which extend from the HIGH point to the periphery of the working region of the cornea are each estimated by a circular arc. Each of these arcs is then corrected in curvature to achieve the required diopter correction at the respective arc. The post-operative corneal surface is then estimated by generating a best-fit surface corresponding to all of the corrected arcs.

BRIEF DESCRIPTION OF THE DRAWINGS

The foregoing brief description, as well as other objects, features and advantages of the present invention will be understood more completely from the following detailed description of presently preferred embodiments, with reference being had to the accompanying drawings in which.

DETAILED DESCRIPTION OF THE PREFERRED EMBODIMENTS

Figure 1:
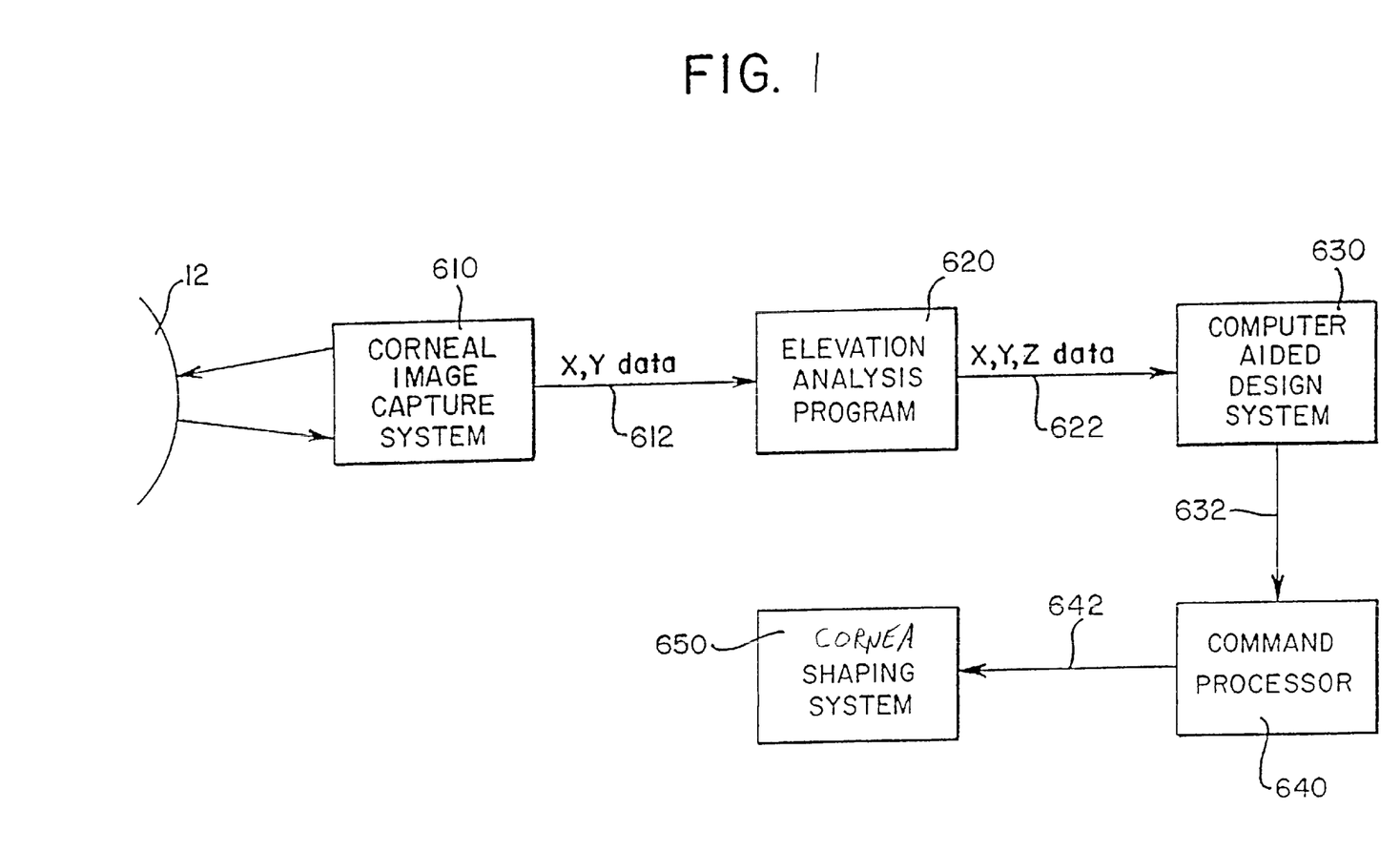
FIG. 1 is a block diagram illustrating a method for achieving laser ablation of the cornea in accordance with the present invention.

A process for achieving laser ablation of the cornea in accordance the present invention is illustrated in block diagram form in FIG. 1. The process makes use of a Corneal Image Capture System 610, an Elevation Analysis Program 620, a Computer Aided Design System 630, a Command Processor 640 and a Cornea Shaping System 650. The Corneal Image Capture System 610, in conjunction with the Elevation Analysis Program 620, generates a three dimensional topographic map of the cornea of the patient. The Computer Aided Design System 630 is used as an aid in editing or modifying the corneal topographic data, to create a surface model, and data relating to the model is sent to a Cornea Shaping System 650 via the Command Processor 640. The Command Processor 640 uses the topographic data describing the surface of the cornea to be shaped from the Computer Aided Design System 630 to generate a sequence of commands/control signals required by the Cornea Shaping System 650. The Cornea Shaping System 650 accepts, from the Command Processor 640, a sequence of commands that describe the three dimensional movements of the Cornea Shaping System (any coordinate system may be used; e.g., Cartesian, radial or spherical coordinates) to shape the cornea.

The Corneal Image Capturing System 610 and the Elevation Analysis Program 620 are preferably components of the PAR® Corneal Topography System ("the PAR® System"), which is available from PAR Vision Systems. The Elevation Analysis Program 620 is a software program executed by a processor, for example an IBM™ compatible PC. Program 620 generates a third dimension element (a Z coordinate representing distance away from a reference plane inside the eye) for each of a plurality of sample points on the surface of the cornea measured by system 610. Each point is defined by its X-Y coordinates as mapped into the reference plane, and its Z coordinate is determined from brightness of the point. One method of calculating the elevation of each point, i.e., the Z coordinate, is by comparing the X-Y and brightness values measured from the patient's cornea 14 with the coordinates and brightness of some reference surface with known elevation, e.g., a sphere of a known radius. The reference values can be pre-stored.

The final output of the Elevation Analysis Program 620 is the X-Y-Z coordinates for a multiplicity of sample points, known as a point cloud, on the surface of the cornea 14. It will be apparent to those skilled in the art that any method can be used that can generate X, Y, Z corneal data providing both location and elevation information for points on the corneal surface with the required accuracy. In the preferred embodiment about 1500 points are spaced in a grid pattern, as viewed in the X-Y plane, so the projections of the points into the X-Y plane are about 200 microns apart.

The X-Y-Z data output from the Elevation Analysis Program 620 can be formatted in any number of well-known machine-specific formats. In the preferred embodiment, the data are formatted in Data Exchange File (DXF) format, an industry standard format which is typically used for the inter-application transfer of data. A DXF file is an ASCII data file, which can be read by most computer aided design systems.

Figures 2, 3:
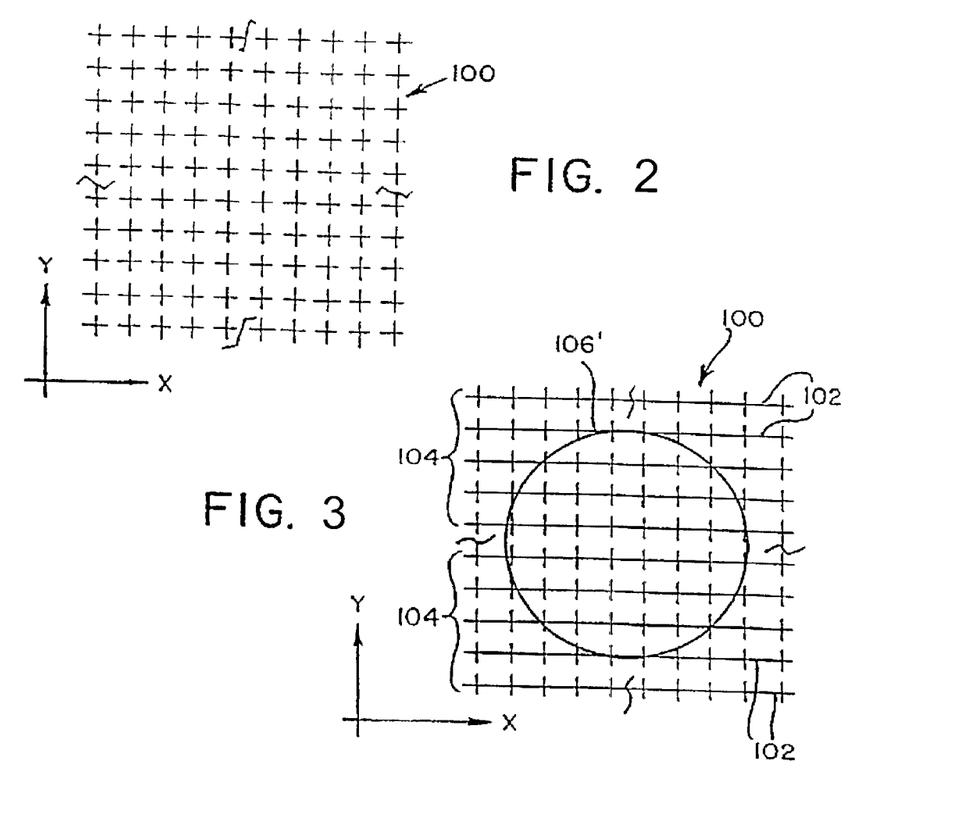
FIG. 2 is a schematic diagram illustrating a plan view of a point cloud as obtained with a corneal image capture system.
FIG. 3 is a schematic plan view similar to FIG. 2 illustrating a plurality of splines and how they are connected through the data points of the point cloud.
Figure 4:
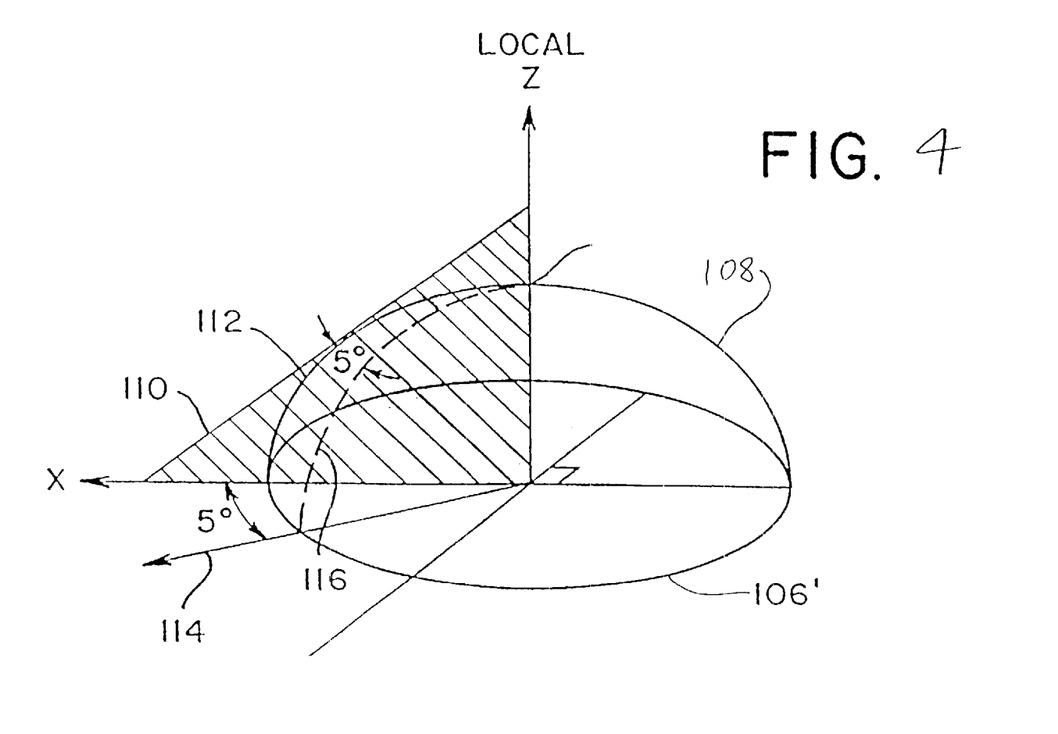
FIG. 4 is a perspective view of a cornea matching surface illustrating how characterizing curves are constructed.

Referring now to FIGS. 2 and 3, a point cloud 100 is depicted as it would appear when viewing the reference plane along the Z-axis (i.e., as projected into the X-Y plane). Each point corresponds to a particular location on the patient's cornea. The data are usually generated from an approximately 10 mm×10 mm bounded area of the cornea, the working area. Thus, there may be as many as 50 rows of data points. A surface 108 (see FIG. 4) that models or matches the topography of the surface of the patient's cornea is generated by the computer aided design system 630 from the data points generated by the Elevation Analysis Program. In a preferred embodiment, Computer Aided Design System 630 is the Anvil 5000™ program which is available from Manufacturing Consulting Services of Scottsdale, Ariz.

Cornea matching surface 108 is preferably produced by first generating a plurality of splines 102, each defined by a plurality of the data points of the point cloud 100. The generation of a spline that intersects a plurality of data points (i.e., knot points) is, per se, known to those skilled in the art and can be accomplished by the Anvil 5000™ program once the input data have been entered. For more information regarding the generation of a surface model, see U.S. Pat. No. 5,807,381, the disclosure of which is incorporated herein by reference. In a preferred embodiment, the known non-rational uniform B-spline formula is used to generate the splines, but they could be generated by other well-known mathematical formulas for splines, such as the cubic spline formula or the rational uniform B-spline formula. As illustrated in FIG. 3, in a preferred embodiment, each of the splines 102 lies in a plane that is parallel to the X and Z axes and includes a row of points from the cloud 100 in FIG. 3.

Surface 108, which matches the corneal surface of the scanned eye, is then generated from splines 102. There are a number of well-known mathematical formulas that may be used to generate a surface from a plurality of splines 102. In the preferred embodiment, the well known nurb surface equation is used to generate a corneal surface from splines 102. In the embodiment, because the scanned area of the eye is approximately 10 mm×10 mm, approximately 50 splines 102 are created. As illustrated in FIG. 3, a skin surface segment 104 is created for a small number (e.g., five) of the adjacent splines. Adjacent skin surface segments 104 share a common border spline. Thus, about ten skin surface segments are generated from the point cloud and are then merged together by the Anvil 5000™ program in a manner known to those skilled in the art, to produce one composite surface 108.

Neither the original data points, nor the knot points of splines 102 necessarily lie on surface 108, owing to the mathematical generation of the surface when using the nurb surface equation formula. However, the surface 108 estimates those points within a predefined tolerance.

The HIGH point on the generated corneal matching surface 108 (i.e., the point having the greatest Z value) is determined. A cylinder 106 of a predetermined diameter, is then projected onto the corneal matching surface 108 along an axis which is parallel to the Z-axis and passes through the HIGH point. Cylinder 106 preferably has a diameter of 4 mm–7 mm, typically 6 mm, and the closed contour formed by the intersection of cylinder 106 with surface 108 projects as a circle 106' in the X-Y plane. On the matching surface 108, this contour defines the outer margin 26 of the working area of the cornea. The cornea is the most symmetric and spherical about the HIGH point and, therefore, provides the best optics at this point.

The outer margin 26 must fit within the point cloud, so that the surfaces of the cornea can be formed based on the measured corneal data. The computer aided design system 630 can then illustrate a default circle 106' (in the X-Y plane) with respect to the point cloud, for example on a monitor screen, so that the operator can be assured that circle 106' falls within the point cloud. Additionally, system 630 can be set up to determine if circle 106' falls within point cloud 100 and, if it does not fall completely within point cloud 100, to alert the user to manipulate the circle (i.e., move the center point and/or change the radius of the circle) so that circle 106' lies within the corneal data point cloud 100. In a worst case scenario, the eye should be rescanned if insufficient data is available from the scanned eye to ensure that the cornea will fit properly on the patient's cornea. Alternatively, the area of the point cloud can be made larger.

It is to be understood that circle 106' is only a circle when viewed in the X-Y plane (i.e., looking along the Z-axis). Actually, the periphery 26 is approximately elliptical and lies in a plane which is tilted relative to the reference plane. A line perpendicular to this tilted plane which passes through the HIGH point will be referred to as the "local Z-axis" and the tilt of the tilted plane relative to the reference plane will be considered the tilt angle of the working area of the cornea.

The cornea is about 600 $\mu$m thick. In most corneal ablation procedures, less than 100 $\mu$m depth of cornea is ablated, because there is virtually no risk of scarring with the type of lasers that are typically used. Beyond the 100 $\mu$m depth, the risk of scarring increases. For example, 120 $\mu$m depth ablation is known to cause scarring. However, there exists the possibility that the risk of scarring for deeper ablations may be reduced by drug therapy prior to or contemporaneous with the laser treatment. The magnitude of the corneal undulations is typically about fifteen to twenty microns from the crest of a hill to the trough of a valley and may be as great as about thirty microns.

The proposed use of a collagen gel, for example A Type 1 collagen, to mold a smooth spherical surface on the cornea using a temporary mask allows the cornea to be ablated uniformly to the spherical shape defined by the mask. However, because conventional lenses do not seat themselves predictably about a particular point on the eye, the ablation procedure relying on them will result in not maintaining corneal tilt or proper orientation, because the art has not recognized the need to orient the lens so as to retain corneal tilt, to locate the optical center of the eye at the HIGH point of the cornea, and to maintain proper rotational orientation.

The surgical procedures performed in accordance with the present invention will seek to correct the patient's vision in accordance with the required corrections established in a "refraction test." When this test is performed, the patient sits in chair which is fitted with a special device called a "phoropter", through which the patient looks at an eye chart approximately 20 feet away. As the patient looks into the phoropter, the doctor manipulates lenses of different strengths into view and, each time, asks the patient whether the chart appears more or less clear with the particular lenses in place. In practice, the doctor is able to vary the power or diopter correction about two orthogonal axes, as well as the degree of rotation of those axes about a Z-axis along the line-of-sight. The doctor continues to modify these three parameters until he achieves the optimum vision. The results of the refraction test are usually given in the form "a, b, c°", where "a" is the diopter correction at the first axis, "b" is the additional diopter correction required at the second, orthogonal axis, and "c°" is the angle of rotation of the first axis relative to the horizontal. This form of information is given for each eye and is immediately useful in grinding a pair of lenses for eyeglasses.

For the purposes of the present invention, it is preferred to perform a modified form of refraction test. For this modified form of refraction test, the eye doctor adjusts the phoropter at a series of equally spaced angles, say every 15° from the horizontal, and obtains the optimum refraction at each angle. Typically, the more angles that are measured, the better the results. However, since the refraction measurements can be time consuming, 15° increments, which results in the total of 12 readings seems to be a reasonable number. The manner of using the modified refraction test will be described in detail below.

There will now be described a technique for generating characterizing curves on surface 108, which will be useful below. A plane 110 is constructed which contains the local Z-axis (See FIG. 4). The intersection between plane 110 and surface 108 defines a first characterizing curve 112. Plane 110 is then rotated about the local Z-axis, for example by a 5° increment counterclockwise, as represented by line 114, where its intersection with surface 108 defines a second characterizing curve 116, which is illustrated as a dashed line in FIG. 4. This process continues at fixed rotational increments about the local Z-axis, for example every 5°, until plane 110 has swept 360°, to produce a complete set of characterizing curves, in this case seventy-two (360°±5°).

In accordance with a first embodiment of the present invention, corneal ablation surgery is performed so as to effect the vision corrections specified in a conventional refraction test. This procedure requires the generation of two characterizing curves as described above. The first characterizing curve is obtained by constructing a plane which contains the local Z-axis and forms an angle of c° with the X axis, that is, the rotational angle obtained in the conventional refraction test. The first characterizing curve is formed by the intersection of this plane with the surface 108. The second characterizing curve is obtained by constructing a plane which contains the local Z-axis and is perpendicular to the first plane. The intersection of the second plane with the surface 108 defines the second characterizing curve.

Figure 5:
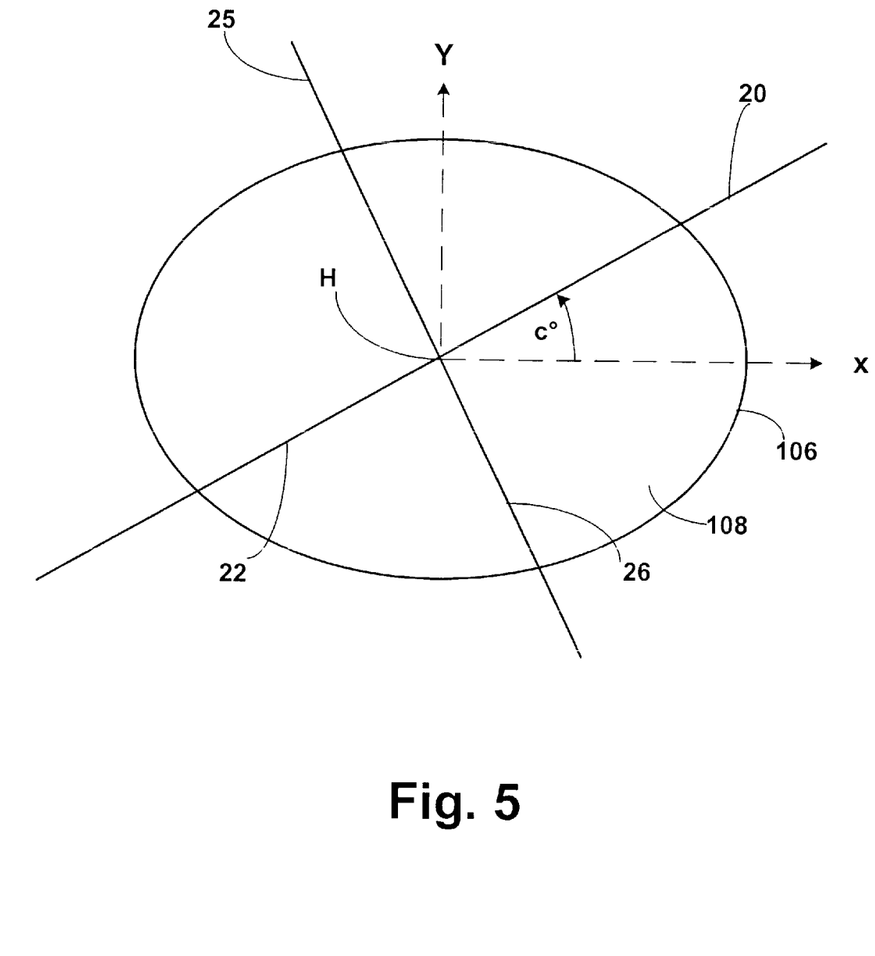
FIG. 5 is a plan view in the tilted plane illustrating how the cornea matching surface is modified to provide vision correction in accordance with a first embodiment.

FIG. 5 is a plan view in the tilted plane of contour 106' illustrating the derivation of these two characterizing curves. The contour 106' is the periphery of the working area of the cornea as it appears in the tilted plane. Plane 20 contains the local Z-axis and therefore the HIGH point H and is also perpendicular to the plane of the contour 106' (the tilted plane). Plane 20 forms angle of c° with the X-axis in the tilted plane. The intersection of plane 20 and surface 108 defines a characterizing curve 22 which touches the contour 106' at two points and passes through the HIGH point H. Plane 25 is constructed so as to be perpendicular to plane 20 and to contain the local Z-axis. Plane 25 therefore also contains the HIGH point and is perpendicular to the plane of contour 106'. The intersection of plane 25 and surface 108 defines a second characterizing curve 26, which touches the contour 106' at two points and passes through the HIGH point H.

Each of the characterizing curves may be estimated by a best-fit spherical arc. One manner of doing this is simply to select a circular arc which passes through the three known points for each curve (i.e. the points at which it touches the contour 106 and the HIGH point. With the radius of curvature of each characterizing curve determined, the Zeiss lens formula provides a diopter value for each characterizing curve. The diopter value "a" is then added to the diopter value for curve 22 and the diopter value "a+b" is added to the diopter value for characterizing curve 25. Those skilled in the art will appreciate that the values a and b may be positive or negative. With the corrected diopter values for curves 22 and 26 determined, the Zeiss lens formula now provides the corrected average radii of curvature for the two curves. The two curves are then replaced by circular arcs having those radii of curvature. A corrected surface model 108' for the cornea is then generated within the bounded area 106' by producing a curve driven surface which interpolates from the circular arc for curve 22 to the circular arc for curve 26, while driving along contour 106'. The generation of curve driven surfaces is a feature available in most CAD/CAM programs. In effect, a surface of rotation is produced which is bounded by contour 106 and is made up of a continuum of circular arcs centered about the HIGH point H and ranging from the arc for curve 22 to the arc for curve 26.

From the above description, it will be appreciated that the corrected corneal surface 108' will conform precisely to the specifications of the refraction test in the two planes 20 and 25 and will vary gradually therebetween. Since all operations were done about the HIGH point and with respect to the local Z-axis, the tilt of the cornea relative to the eye is maintained, as is its general geometry. Only the small area within the contour 106' has been changed in shape in order to achieve the required degree of correction.

Figure 6:
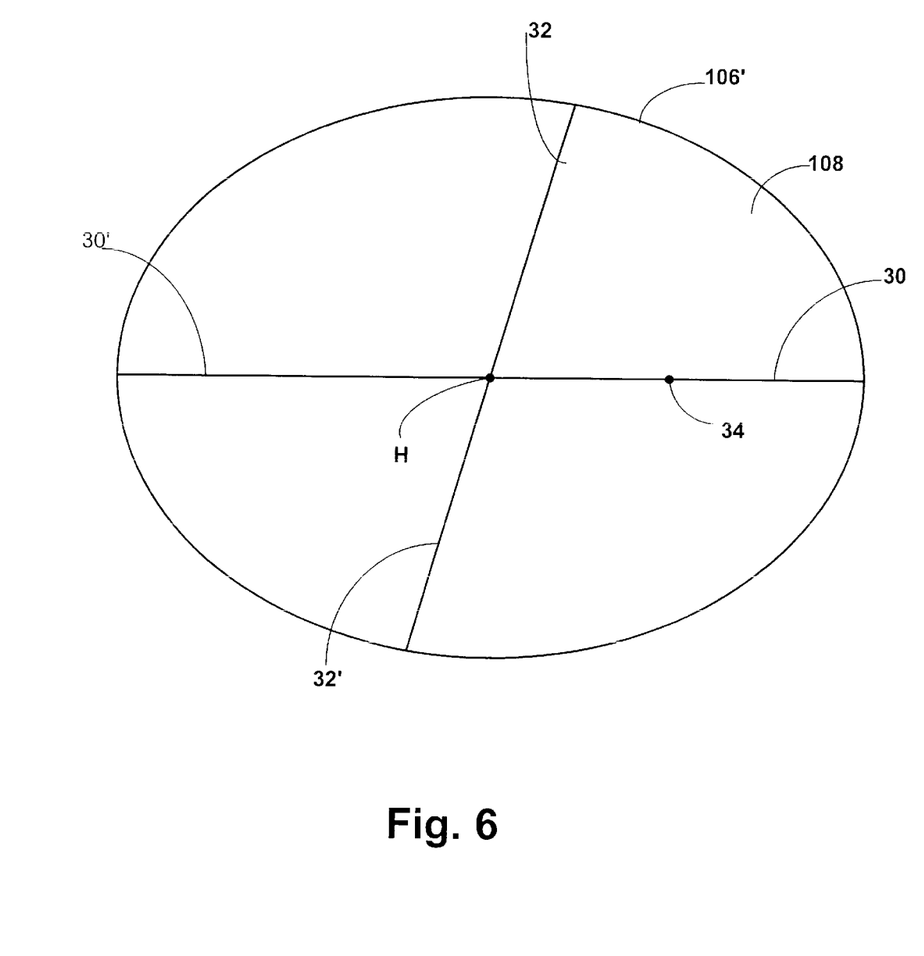
FIG. 6 is a plan view in the tilted plane illustrating how the cornea matching surface is modified in order to achieve vision correction in accordance with a second embodiment.

In accordance with a second embodiment, the area of the surface 108 bounded by the contour 106' is modified in shape in a manner to retain the asymmetry originally present in the cornea. In the manner described above, a multiplicity of characterizing curves (meridians), preferably 72, is obtained about the HIGH point within the contour 106'. The average radius of curvature of each characterizing curve is determined, and the curves with the greatest and smallest radii of curvature (curves 30 and 32, respectively in FIG. 6) are found. The extensions of curves 30 and 32 towards the opposite margins of contour 106 are then created, to define the curves 30' and 32', respectively. FIG. 6 shows the projection of the contour 106' and the curves 30, 30', 32 and 32' into the tilted plane of contour 106'. In each instance, instead of using the average radius of curvature for a curve, the curve may be estimated by a circular arc which passes through the HIGH point, the intersection of the curve with the contour 106', and that point which in FIG. 6 is halfway between those two points (for example, point 34 in contour 30).

Having a radius of curvature for each of the four curves, it is now possible to generate corrected average radii of curvature. In order to do so, use is made of the results of the modified refraction test described above. In each instance, a curve will receive the diopter correction of the arc measurement which is closest to it in the modified refraction test. Each of the arcs 30, 30', 32 and 32' is then replaced by a circular arc having the corrected average radius of curvature, and four curve driven quadrant surfaces are generated. For example, an upper right-hand quadrant surface is generated by driving the circular arc for curve 32 into the circular arc for curve 30 along the contour 106' as a drive rail. This produces a curve driven quadrant surface having a perimeter of the contour 106' which merges smoothly in shape from the arc for curve 32 to the arc for curve 34. The three additional quadrant surfaces are similarly generated, and the interfaces between the surfaces are smoothed, to produce the finished, corrected surface model 108' bounded by the contour 106'.

It should be appreciated that the preceding construction of model 108' can be undertaken even if the only test results available are those from a conventional refraction test. The required correction at each of arcs 30, 30', 32 and 32' would then be determined by interpolation. For example, suppose arc 30 extended 20° beyond c° (the refraction test angle), the interpolated diopter correction for arc 30, $d_{30}$ could be computed as:

$$d_{30} = a + \frac{20}{90}b.$$

The remaining diopter corrections could be determined similarly by interpolation. The corrected surface model 108' would then be generated the same manner as described above relative to FIG. 6.

The surface model 108' achieves the required correction along four different arcs, while conforming more closely to the original shape of the cornea than the model of FIG. 5. Specifically, it has retained the original asymmetry of the cornea.

In accordance with a third embodiment, the required correction of vision is achieved by modifying the curvature of the cornea while retaining its overall original shape. For this embodiment, it would be preferred to perform the modified refraction test at a multiplicity of angles and to generate the characterizing curves at the same multiplicity of angles. However, the procedure can be performed using the results of a conventional refraction, as will be explained below.

Preferably, the characterizing curves and refraction measurements are taken at every 5°, so that there will be a total of 72 characterizing curves. As was the case with the second embodiment, the average radius of curvature of each curve is determined, and the required diopter correction is applied to each curve, to obtain a corrected average radius of curvature. Each characterizing curve is then replaced by a circular arc having the corrected average radius of curvature, and the corrected surface model is generated by interpolating between all of the corrected circular arcs. Smoothing is then applied to produce the corrected surface model within the bounding contour 106'. This surface model will not only include the required diopter correction, but will closely approximate the original shape of the cornea as well.

The present procedure can be performed even if the only available test results for vision correction are a conventional refraction test. As was done for the second embodiment, the diopter correction at each of the 72 arcs can be computed by interpolating between the conventional refraction test measurement a and b. The procedure then continues as already described.

Once the desired corrected surface model 108' within the contour 106' is obtained, Computer Aided Design system will provide information to Command Processor 640 which will permit it to generate appropriate control signals for operating the Cornea Shaping System 650. Preferably, system 670 produces information which represents the differences between models 108 and 108', so that the appropriate material may be removed from the cornea. Typically, when selective corneal ablation is being performed, system 650 will include a station in which the patient's head and eyes are held in a fixed manner, and a high precision laser is maintained in close registry with the cornea so as to achieve precise movement and controlled degrees of ablation. Preferably, the laser is a spot laser which is moved to precise locations under control of Command Processor 640 and is then precisely controlled to apply the required degree of ablation at each location.

The components utilized to achieve the process depicted in FIG. 1 can prove costly and not within the budget of the average doctor's office. It is therefore contemplated that corneal shaping could, alternately, be performed by a process of uniform ablation utilizing a smoothing mask. As will be explained below, the mask is shaped by the posterior surface of a contact lens which has been formed to conform to the corrected matching surface 108'. Uniform ablation with an inexpensive laser to the maximum thickness of the mask will then result in appropriate shaping of the working area of the cornea. Moreover, this process is performed with an inexpensive wide beam laser and can be done relatively slowly so as to eliminate the need for extreme precision.

It should also be appreciated that when uniform ablation is performed, the only steps performed by the doctor preliminary to ablation would be the eye test. The patient would then be sent to a laboratory which would have all of the equipment illustrated in FIG. 1. The laboratory would generate the precision contact lenses for molding the mask and furnish them to the doctor. The uniform corneal ablation could then take place in the doctor's office.

Figure 7:
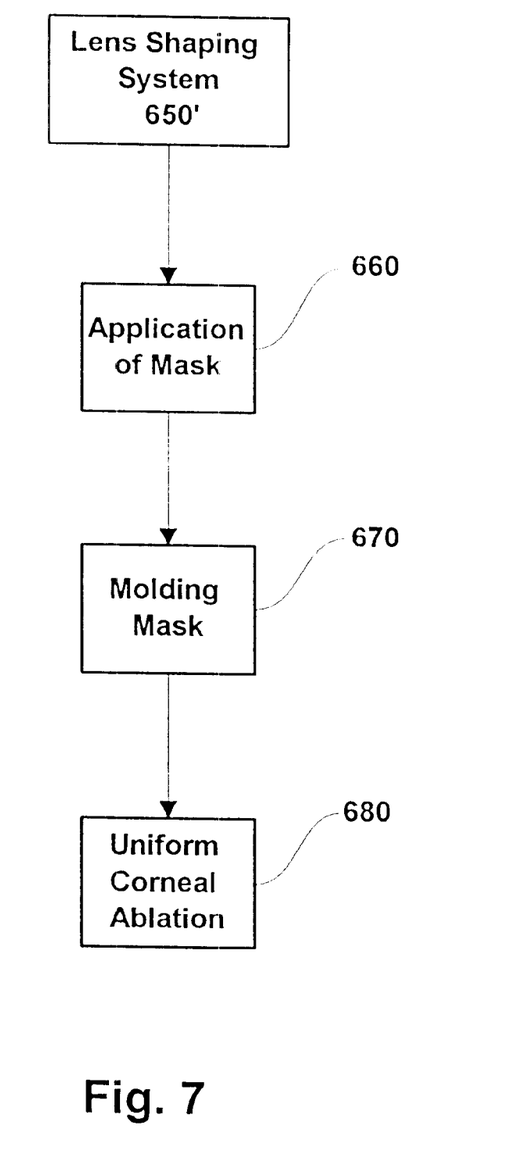
FIG. 7 is a functional block diagram illustrating how corneal shaping is achieved when using a moldable mask and uniform corneal ablation.

From the preceding description, it will be appreciated that, in the case of uniform corneal ablation, the block diagram of FIG. 1 is modified as illustrated in FIG. 7. That is, the elements of FIG. 7 represent the contents of block 650 (Cornea Shaping System). Block 650' is a Lens Shaping System. Systems for making custom contact lenses are well known. In this case, the contact lens could be provided with appropriate markings to guide the doctor in orienting the lens. Alternatively, the lens could be made with a custom peripheral skirt portion to assure that it will orient itself on the patient's cornea in a predetermined position and orientation. Lenses of this type and their method of manufacture are disclosed in U.S. Pat. No. 5,502,518 issued Mar. 26, 1996, the disclosure of which is incorporated herein by reference.

Figure 8:
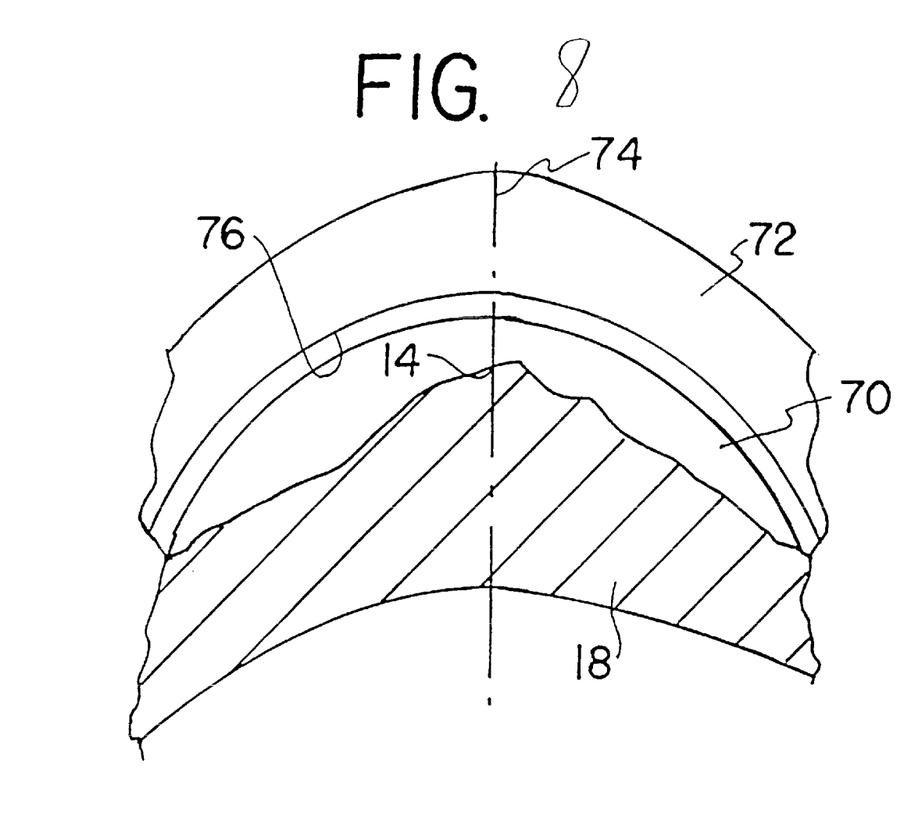
FIG. 8 is a sectional side view illustrating the application of a contact lens to form a moldable mask when performing uniform corneal ablation.

Once a corrected corneal surface model 108' has been generated, a contact lens 72 (see FIG. 8) having a posterior surface 76 shaped to conform to the corrected corneal surface 108' can be made. Uniform ablation can be performed by depositing a moldable mask 70 onto the cornea 18 (block 660 in FIG. 7), and placing the posterior surface 76 of lens 72 over the moldable mask 70 with correct rotational orientation and so that the optical center 74 of the lens 72 aligns with the HIGH point H. The moldable mask 70 is then molded to the shape of the posterior surface 76 of the lens as the lens is pressed into it (block 670 in FIG. 7).

A presently preferred material for the mask 70 is A Type 1 collagen. The collagen mask is heated-to a temperature of about 42° C. to 45° C. so that it assumes a syrup-like viscosity. The heated collagen is deposited as a film on the cornea where it immediately begins to cool to body temperature (37° C.) at which temperature it assumes a gel-like consistency. Prior to cooling, the lens 72 is positioned on the collagen film as explained above and illustrated in FIG. 7. Once the collagen gel has cooled and set, the positioned lens 72 will have molded the collagen into a surface having the desired corrected shape of the cornea. The lens 72 can then be discarded.

The cornea plus collagen gel have a smooth, undulation free surface. Uniform ablation of the masked anterior surface of the cornea (block 680 in FIG. 7) can then proceed by ablating the masked cornea to a depth sufficient to remove all of the gel, in a manner known to those skilled in this art. Because the collagen and cornea ablate at the same rate (they are virtually identical materials, hence the preference for this material), uniform ablation will result in a smooth corneal surface of the desired shape.

For reasons already explained, the collagen mask is preferably formed with a width of 6 mm, and a 1 mm lip including a transition region. This transition region may be formed in a separate step, or the posterior surface of the contact lens may be ground so as to have a properly shaped transition lip.

Figure 9:
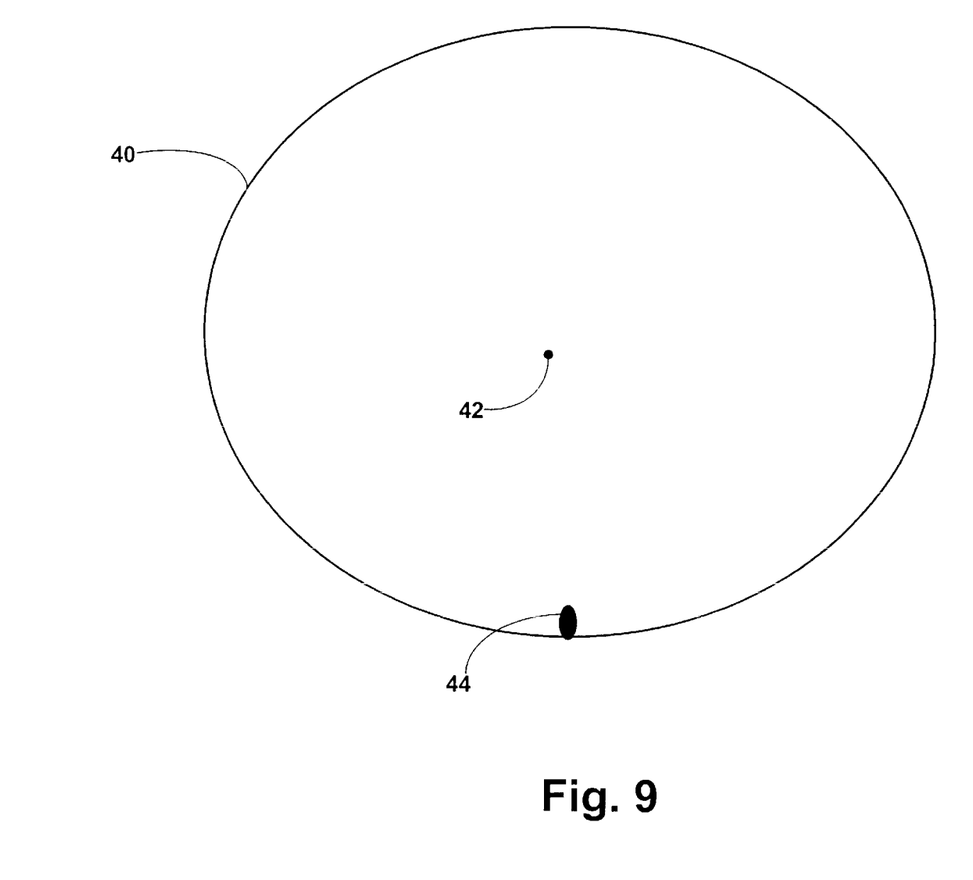
FIG. 9 is a plan view of a contact lens usable to form the moldable mask for uniform corneal ablation, which contact lens is manually positioned.

FIG. 9 illustrates one form of contact lens 40 useful in forming the collagen mask when performing uniform ablation. The lens is formed as described above by conventional lens manufacturing techniques, such as molding or shaping on a lathe. When the original corrected model 108' of the cornea is produced, the operator also defines a point on the cornea which corresponds to the center of the pupil. When the lens is manufactured, a visible index marking 42 is placed at the location on the anterior surface of the lens which should cover the center of the pupil. Similarly, during manufacture of the lens, a visible index marking 44 is placed at the bottom edge of lens 40 or, alternatively, at one of the apexes at the corner of the eye, or any other predefined orientation. In positioning lens 40 over the collagen on the patient's eye, the doctor locates index 42 over the center of the pupil and assures that index 44 is pointing downward (or any other predefined orientation). Lens 40 will then be positioned properly over the HIGH point of the cornea with the proper rotational orientation. Pressing the lens into the collagen will then shape it appropriately.

Figure 10:
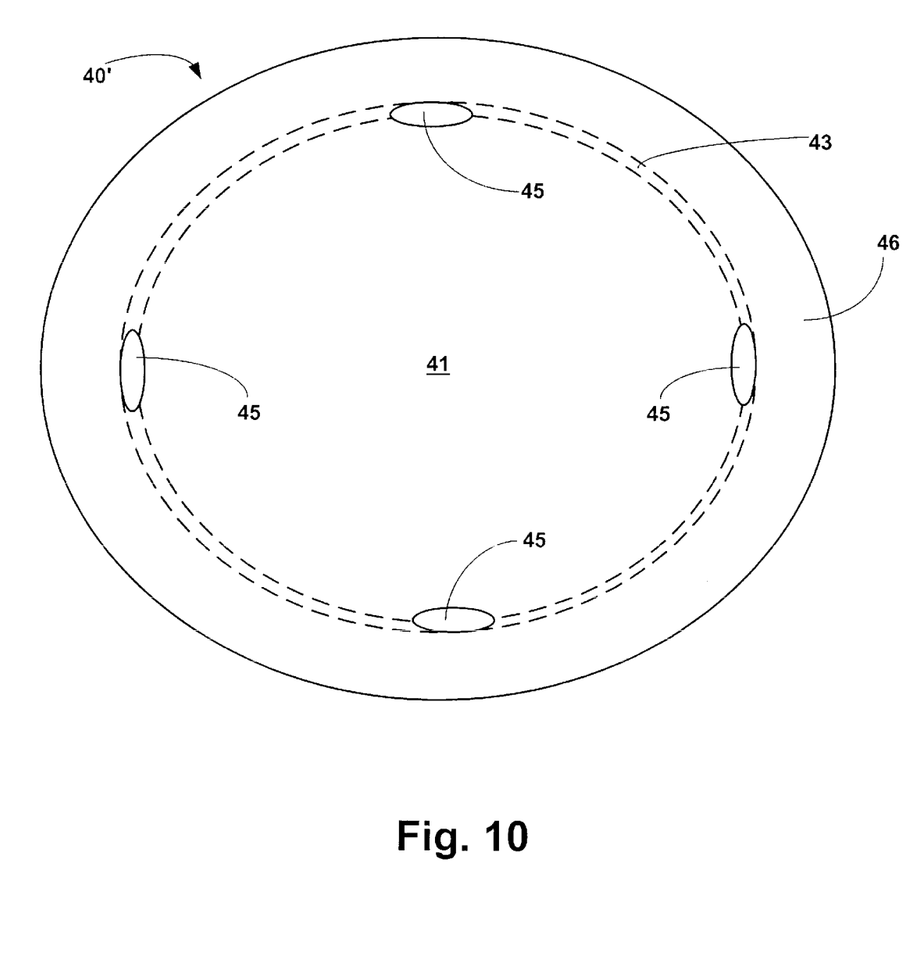
FIG. 10 is a plan view of a contact lens similar to the lens of FIG. 9, except that the lens is constructed to position itself automatically upon being applied to the eye.

FIG. 10 illustrates a contact lens 40' which may be used to shape the collagen mask, in the event that more precision in orientation is required than can be obtained manually. The lens includes a central portion 41, the posterior surface of which is constructed to achieved the desired shaping of the collagen mask. Surrounding the central portion in the posterior surface of the lens is a channel 43. The lens may be formed with a ridge, to allow the channel 43 to be deeper. At spaced locations along the channel 43, there are provided openings 45, which extend through the lens. Four spaced openings are illustrated, but it will be appreciated that a larger or smaller number may be provided. Outward of the channel 43, lens 40' includes a peripheral skirt 46, the posterior surface of which is designed to conform closely to the shape of the surface of the cornea outside the working area. As explained above, the construction of the skirt is intended to make the lens 40' position itself automatically on the cornea in a predetermined position and orientation.

The lens is applied immediately after the collagen material is placed on the cornea. The skirt will assure automatic alignment of the lens and, as the center portion 41 is pressed down, the thinned out material of the channel 43 allows a certain amount of rearward movement of the central portion relative to the skirt. When the posterior surface of portion 41 of the lens comes into contact with the collagen, it will force it to spread out and flow into the channel 43, then out of the channel through the openings 45. Excess material exiting from the openings 45 may be wiped away immediately. When the central portion 41 is fully depressed, the collagen material has been appropriately shaped for the ablation process. The lens 40' may then be removed and discarded.

Figure 11:
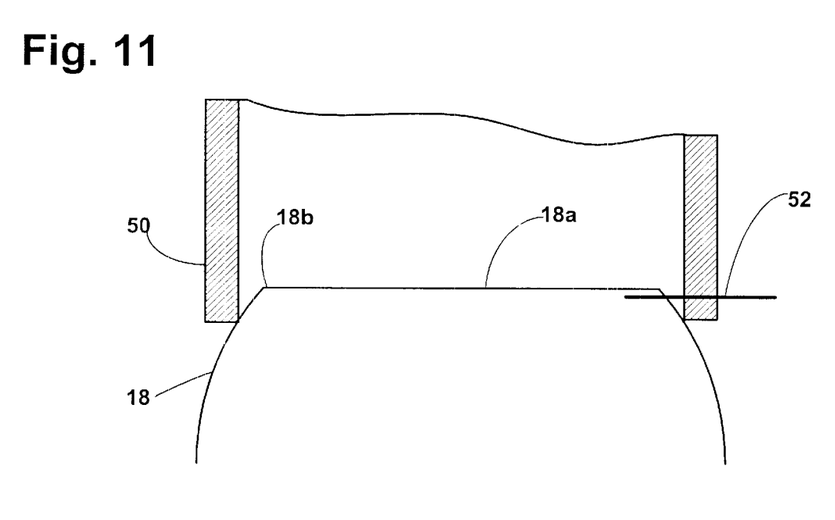
FIG. 11 is a side view, with parts in section, illustrating applanation of the cornea during Lasik surgery.

Another form of selective laser ablation surgery which is commonly used for corneas requiring removal of a relatively large amount of material is known as laser assisted interstromal kerotoplasty (hereafter referred to as "Lasik".) The method for performing conventional Lasik surgery is illustrated schematically in FIG. 11. It is performed with the aid of an instrument called a microkeratome, which includes a vacuum cylinder 50 which is positioned over the cornea 18. In practice, a fitting is provided (not shown) which is centered over the pupillary axis and the cylinder is attached to the fitting. Typically, the microkeratome is positioned over the cornea with its axis aligned with the pupillary axis. A strong vacuum is then applied to the cylinder 50 which draws the cornea into the cylinder and simultaneously causes it to flatten or "applanate". Following applanation, a blade 52 is passed beneath the applanated portion 18a of the cornea and parallel to it. Preferably, a cut is made in the cornea approximately 180 μm thick. The cut stops short of the remote end 18b of the applanated portion 18a, leaving an attached, thin flap of corneal material 18c (see FIG. 12). Air is then admitted into the cylinder 50, and the microkeratome is removed, allowing the cornea to return to its normal shape. The flap 18c is then folded back and corneal ablation surgery is performed on the underlying, exposed surface of the cornea. The reason for performing this form of surgery is that the corneal surface under the flap 18c is less likely to form scar tissue. Upon completion of corneal ablation, the flap c is carefully folded back down over the underlying surface of the cornea and, upon healing will form a integral, reshaped cornea.

Figure 12:
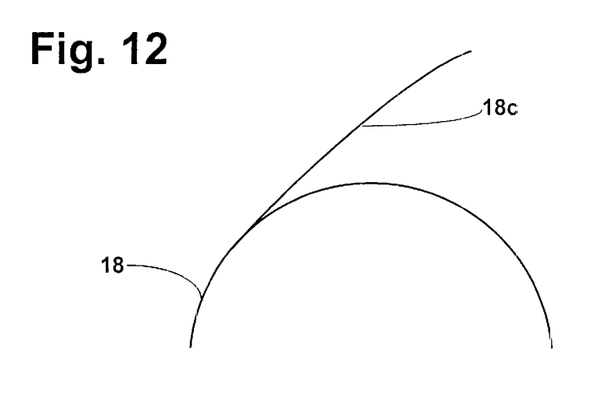
FIG. 12 is a side view illustrating the cornea after creation of a corneal flap, but prior to laser ablation during Lasik surgery.

The theory behind Lasik surgery is that the flap 18c is of uniformed thickness. Therefore, the underlying cornea may be formed to the desired shape and will retain that shape when the flap 18c is replaced. However, since Lasik surgery is performed by taking a slice perpendicular to the pupillary axis, it does not take account of corneal tilt.

As a result, the flap 18c exhibits a substantial amount of variation in thickness. Thus, when flap 18c is replaced over a cornea ablated in the conventional manner, it actually changes the shape of the cornea. The results obtained with traditional Lasik surgery are therefore far from predictable.

It is should be noted that, since, in accordance with the present invention, selective ablation surgery is performed by operating over the working area of the cornea in order to change curvature at every location, and not to produce a particular resulting shape, having a flap 18c with an irregular thickness will not affect the outcome of the surgery. That is, since each point on the area underlying the flap 18c is ablated to achieve the desired correction or change and not a desired overall shape, when the flap 18c is replaced, the desired changes will, in fact, be achieved in the overall cornea.

Figure 13A:
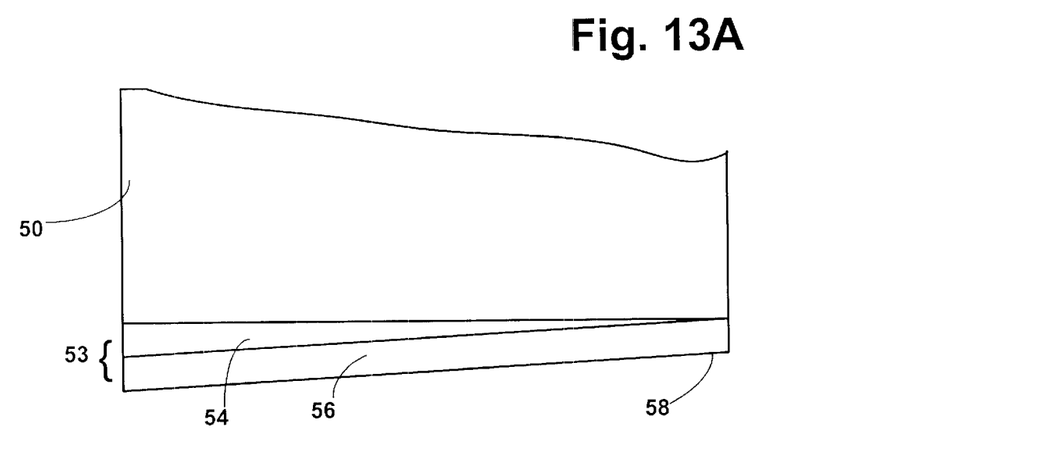
FIG. 13A is a side view illustrating an improvement to a conventional microkeratome in accordance with the present invention.
Figure 13B:
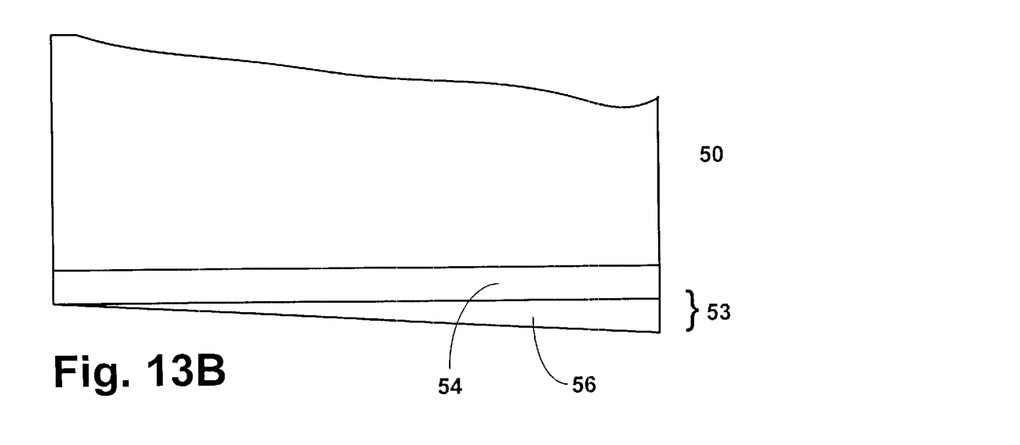
FIG. 13B is a left side view with respect to FIG. 13A.
Figure 13C:
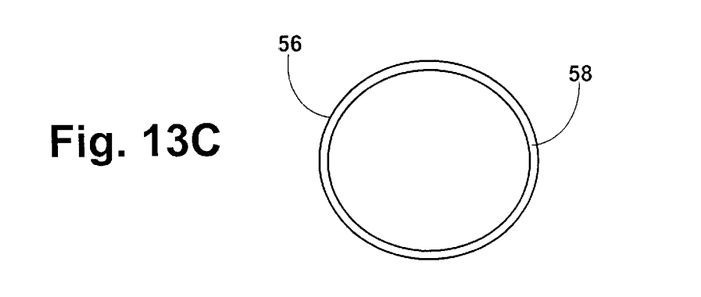
FIG. 13C is a plan view of one of the rings forming part of assembly 53 in FIGS. 13A and 13B.

However, having a flap 18c with uneven thickness is still undesirable, in that certain areas may be excessively thin. Accordingly, in accordance with the present invention, certain modifications are made to the microkeratome cylinder to cause the flap 18c to be cut so that it takes account of the tilt of the cornea. Referring to FIGS. 13A and 13B, there are shown two schematic diagrams of a microkeratome cylinder including the modification proposed by the applicants. It should be kept in mind that FIG. 13B shows the same apparatus as FIG. 13A, but as seen when looking from the left in FIG. 13A. The present improvement constitutes the addition of a shim apparatus 53 at the bottom of the cylinder 50. In actuality, the apparatus 53 would be mounted between the bottom of the cylinder and the fitting that holds it to the cornea. As can be seen, the shim apparatus preferably comprises two rings, 52, 56 which are tapered in thickness. The ring 54 is designed to be secured to the bottom of cylinder 50, as by complimentary screw threads or a bayonet connection, both of which are well-known to those skilled in the art. Similarly, ring 56 is designed to be secured at the bottom of ring 54, as by complementary screw threads or bayonet connection. As can be seen in FIGS. 13A and 13B, the rings 54, 56 are preferably constructed so that their tapers form solid angles which are rotationally perpendicular to each other about the local Z-axis. That is, one provides the solid angle or tilt relative to the X-axis, whereas the other provides the solid angle or tilt relative to the Z-axis.

When using the shim apparatus 53, the doctor would be aware of the corneal tilt of each eye relative to the X- and Y-axes, based upon the results of the corneal model 108. He would then select a ring 54 to give him the appropriate X tilt and a ring 56 to give him the Y tilt and mount them at the bottom the cylinder 50. When fully mounted, the rings provide a lower lip 58 below the cylinder 50 which is tilted relative to the bottom of the cylinder in the same manner that the cornea is tilted. When the doctor subsequently applies the cylinder 50 to the cornea, the shimming device 52 causes the entire cylinder to be tilted in conformity with the corneal tilt. The knife 52 then performs its cut with the same tilt, avoiding substantial irregularities in thickness of the flap 18c.

Although preferred embodiments of the invention have been disclosed for illustrative purposes, those skilled in the art will appreciate that many additions, modifications and substitutions are possible, without departing from the scope and spirit of the invention.

What is claimed is:

1. A method for treating the cornea of an eye to improve vision, said method being performed with the aid of a computer system running a topological modeling computer program which, making use of sampled points on the cornea for which the coordinates are known relative to a reference plane, produces a surface model of said cornea which closely represents the surface of the cornea, said method comprising the steps of:

modifying the shape of the surface model enough to change the radius of curvature at a plurality of selected points to achieve a correction in vision indicated to be necessary by an eye test, without introducing substantial changes in shape that are not associated with changing the radius of curvature, to produce a corrected surface model; and utilizing the corrected surface model to control the shape of at least a portion of a surface of a contact lens for use in the eye.

2. In a method for treating the cornea of an eye to improve vision, said method being performed with the aid of a computer system running a topological modeling computer program which, making use of sampled points on the cornea for which the coordinates are known relative to a reference plane, produces a surface model of said cornea which closely represents the surface of the cornea, said method comprising the steps of:

defining the periphery of a working area of the cornea by the intersection between the surface model and a cylinder of predefined diameter, the axis of which is perpendicular to the reference plane and passes through the point on the surface model, the HIGH POINT, which is most distant from the reference plane;

defining the LOCAL Z AXIS as a line passing through the HIGH POINT which is perpendicular to a plane that most closely contains the periphery of the working area;

creating a plurality of characterizing curves each defined by the intersection with said surface model of a plane containing the LOCAL Z AXIS, the plane being in different rotational positions about the LOCAL Z AXIS for at least two of the characterizing curves;

modifying the shape of the at least two characterizing curves so that the radius of curvature therealong is changed in accordance with the diopter correction required at the at least two characterizing curves as previously determined from a vision test performed on the eye;

constructing a corrected surface model in which the portion of the surface bounded by the periphery of the working area matches the at least two modified characterizing curves and varies smoothly therebetween; and utilizing the corrected surface model to control the shape of at least a portion of a surface of a contact lens for use in the eye.

3. The method of claim 2 wherein the modifying step comprises substituting for one of the at least two characterizing curves a circular arc which has a radius equal to the average radius of curvature along the one characterizing curve.

4. The method of claim 2 wherein the constructing step comprises producing a curve driven surface between a pair of the at least two modified characterizing curves using the portion of the periphery of the working area lying therebetween as the drive rail.

5. The method of claim 2 wherein two characterizing curves are utilized and the curves are oriented in rotational positions relative to the LOCAL Z AXIS which correspond to the orientation of two axes given in a conventional refraction test of the eye, the modifying step being performed so that the curvature on each characterizing curve is changed as required by the diopter correction indicated by the refraction test for a corresponding axis of the eye test.

6. The method of claim 2 wherein four characterizing curves are utilized, all extending between the HIGH POINT and the periphery of the working area, a selected two of the curves corresponding, respectively, to the potion of the surface model having the greatest curvature and the portion of the model having the least curvature, the other two characterizing curves each being a continuation of one of the selected curves through the HIGH POINT and to the periphery of the working area, whereby the surface model retains any rotational asymmetry of the cornea.

7. The method of claim 2 wherein a multiplicity of characterizing curves are utilized, all extending between the HIGH POINT and the periphery of the working area, the modifying step comprising providing to each characterizing curve a corresponding amount of diopter correction indicated by a test of the eye, whereby the inherent shape of the cornea is closely conformed to in the corrected surface model.

8. A contact lens comprising a surface shaped to conform to a modified surface model derived from a surface model of said cornea which closely represents the surface shape of the cornea by modifying the shape of the surface model enough to change the radius of curvature at a plurality of selected points to achieve a correction in vision indicated to be necessary by an eye test, without introducing substantial changes in shape that are not associated with changing the radius of curvature.

9. A contact lens comprising a surface shaped to conform to a modified surface model derived from a surface model of said cornea which closely represents the surface shape of the cornea by modifying the shape of the surface model enough to change the radius of curvature at a plurality of selected points to achieve a correction in vision indicated to be necessary by an eye test, without introducing substantial changes in shape that are not associated with changing the radius of curvature, further comprising a peripheral skirt portion on the lens having a posterior surface conforming closely to the topology of the cornea, whereby the lens is self-orienting relative to the eye.

* * * * *